US010314481B2

(12) United States Patent
Han

(10) Patent No.: US 10,314,481 B2
(45) Date of Patent: Jun. 11, 2019

(54) APPARATUS FOR RETINOSCOPY

(71) Applicant: Jeong-Woo Han, Suwon-si (KR)

(72) Inventor: Jeong-Woo Han, Suwon-si (KR)

( * ) Notice: Subject to any disclaimer, the term of this patent is extended or adjusted under 35 U.S.C. 154(b) by 201 days.

(21) Appl. No.: 15/305,097

(22) PCT Filed: Apr. 13, 2015

(86) PCT No.: PCT/KR2015/003650
§ 371 (c)(1),
(2) Date: Oct. 19, 2016

(87) PCT Pub. No.: WO2015/163616
PCT Pub. Date: Oct. 29, 2015

(65) Prior Publication Data
US 2017/0042420 A1 Feb. 16, 2017

(30) Foreign Application Priority Data

Apr. 25, 2014 (KR) ........................ 10-2014-0049820

(51) Int. Cl.
*A61B 3/14* (2006.01)
*A61B 3/103* (2006.01)
*A61B 3/00* (2006.01)
(52) U.S. Cl.
CPC ............ *A61B 3/103* (2013.01); *A61B 3/0041* (2013.01); *A61B 3/0075* (2013.01); *A61B 3/0083* (2013.01); *A61B 3/14* (2013.01)
(58) Field of Classification Search
CPC ... A61B 3/0041; A61B 3/0058; A61B 3/0075; A61B 3/0083; A61B 3/0091;
(Continued)

(56) References Cited

U.S. PATENT DOCUMENTS

| 6,456,787 | B1 | 9/2002 | Matsumoto et al. | |
| 2007/0153667 | A1* | 7/2007 | Mihashi | A61B 3/032 369/125 |
| 2013/0265544 | A1* | 10/2013 | Jaeken | A61B 3/103 351/206 |

FOREIGN PATENT DOCUMENTS

| CN | 2238019 Y | 10/1996 |
| CN | 202636906 U | 1/2013 |

(Continued)

OTHER PUBLICATIONS

International Search Report for PCT/KR2015/003650 dated May 21, 2015 from Korean Intellectual Property Office.

*Primary Examiner* — Mustak Choudhury
(74) *Attorney, Agent, or Firm* — Revolution IP, PLLC

(57) ABSTRACT

The present invention provides a retinoscope comprising: a refractor that has a lens module therein and is located at a predetermined distance from eyes of a person to be tested such that a line of sight of the person to be tested passes through an optometry window, wherein the lens module is configured such that a plurality of lenses necessary for correction are selectively located on the optometry window in order to obtain a correction value for correcting the eyes of the person to be tested; a main body for supporting the refractor; a retinoscope unit coupled to one surface of the main body and maintained at a predetermined distance from the refractor, wherein the retinoscope unit radiates light beams to the eyes of the person to be tested so as to be close to the line of sight of the person to be tested and rotates or reciprocates the light beams when receiving a signal of an operating unit; and the operating unit that operates driving of the refractor and the retinoscope unit.

10 Claims, 4 Drawing Sheets

(58) Field of Classification Search
CPC ........... A61B 3/024; A61B 3/032; A61B 3/13;
A61B 3/14; A61B 3/102; A61B 3/103;
A61B 3/132–3/135; A61B 3/145; A61B
3/152–3/158; A61B 3/1035; A61B
3/1208; A61F 9/007; A61F 9/00727;
G02B 21/0012; G02B 21/084; G06F
3/013; G06F 3/0481
USPC ....... 351/205–207, 211, 212, 216, 221, 246;
345/428, 419, 426; 348/164, 169, 173;
369/125; 382/118
See application file for complete search history.

(56) References Cited

FOREIGN PATENT DOCUMENTS

| | | | |
|---|---|---|---|
| JP | 05076496 | A | 3/1993 |
| JP | 2001-149317 | A | 6/2001 |
| KR | 10-2005-0053259 | A | 6/2005 |
| KR | 10-2013-0010079 | A | 1/2013 |

\* cited by examiner

APPARATUS FOR RETINOSCOPY

CROSS REFERENCE TO PRIOR APPLICATIONS

This application is a National Stage Application of PCT International Patent Application No. PCT/KR2015/003650 filed on Apr. 13, 2015, under 35 U.S.C. § 371, which claims priority to Korean Patent Application No. 10-2014-0049820 filed on Apr. 25, 2014, which are all hereby incorporated by reference in their entirety.

TECHNICAL FIELD

The present invention relates to a retinoscope, and more particularly, to a retinoscope capable of deriving an objective and accurate examination value and improving convenience of an examination.

BACKGROUND ART

In general, retinoscopy is an examination method in which certain light beams in front of an examinee are projected into an eye and a pupil of an examinee so that an examiner observes a refractive state of reflected light beams which are reflected from the pupil to find a far point location of the eye of the examinee.

A tool used for the retinoscopy is a retinoscope, and types of retinoscope include a spot retinoscope and a streak retinoscope. Here, the streak retinoscope is widely used since the spot retinoscope has difficulties in examining astigmatism and axis.

As shown in FIG. 1, in a refraction examination using a conventional retinoscope, a distance for an optometric examination between an examinee and an examiner is fixed in a range of 50 cm to 67 cm, a rack lens is located at about 12 mm in front of the eye of the examinee, and then the examinee is instructed to keep the eye on an eye chart from a long distance (5 m). At this point, the examination has to be performed in a state in which the examinee is keeping the eye on the eye chart from a long distance to minimize intervention of control. Accordingly, the examiner has to make an examination at a tilted angle, thus not blocking a line of sight of the examinee. That is, while the line of sight of the examinee passes by the ear of the examiner, the examiner uses his or her right hand and right eye when examining the right eye of the examinee, and uses his or her left hand and left eye when examining the left eye of the examinee, thereby minimizing dislocation of the line of sight as much as possible.

A refraction examination using such a conventional retinoscope has a great effect of suppressing the intervention of control of the examinee and serves as a useful examination method when communication between the examiner and the examinee is not smooth.

However, if dislocation of the line of sight of the examiner and the line of sight of the examinee is large, an error occurs as a measurement is taken away from the center of a cornea. Hence, there has been a problem in that the larger the error, the harder it is to perform an accurate examination.

Further, since the examiner has to observe reflected light beams reflected from a small pupil of the examinee at a distance for an optometric examination in a range of 50 cm to 67 cm, it is not easy to observe the reflected light beams. In particular, if the examinee has a small pupil, it is harder to observe the reflected light beams, thereby increasing eye strain of the examiner. Further, when the examiner is old or has poor vision, an accurate examination is difficult to be performed.

Further, since the examiner has to use his or her right hand and right eye when examining right eye of the examinee and has to use his or her left hand and left eye when examining left eye of the examinee, the examiner feels uncomfortable with examination posture when examining the other side, depending whether the examiner is a right-hander or a left-hander. There has also been a problem in that the examiner with a tremoring hand cannot perform a refraction examination.

Further, there has been a problem in that it is hard to maintain a predetermined distance for an optometric examination with the examinee. Here, diopter of a correction lens is 2 D when the distance for an optometric examination is 50 cm, and 1.5 D when the distance for an optometric examination is 67 cm. While applying diopter with a distance for an optometric examination of 50 cm, if an actual distance for an optometric examination is 50 cm or more or 50 cm or less, an error of 0.25 D unit may occur since a displacement unit of the lens is 0.25 D. Such an error reduces accuracy of the examination, and therefore, it is important to maintain the predetermined distance for an optometric examination.

Further, there is a problem in that it is hard to maintain a predetermined distance between the eye of the examinee and a rack lens located in front of the eye. For example, in the case of a retinoscopy lens with 7.00 D, even though location of the lens changes by only 5 mm, a change of 0.25 D occurs. Therefore, since a predetermined distance between the eye and the rack lens has to be maintained at 12 mm, accuracy of the examination is reduced when the rack lens is located in front of the eye of the examinee by roughly estimating distance.

While such a manual refraction examination has a great effect of suppressing the intervention of control of the examinee and serves as a useful examination method when communication between the examiner and the examinee is not smooth, location adjustment and an examining posture are very difficult, and considerable effort and time are required to be skillful with the examination method. In addition, since the examination is performed manually, an error occurs easily, and further, an accurate examination value cannot be obtained since the examination is done in a subjective manner that can only be performed by a skilled person. Further, it is inconvenient that the examination has to be performed with the rack lens changing in the course of the examination.

Recently, an auto-refractometer has been provided to measure refractive errors simply and rapidly.

The auto-refractometer has advantages of diagnosing refractive errors of an examinee and finding prescribed power for correcting the refractive errors based on the diagnosed information rapidly and precisely, however, due to intermittent error occurrence, the retinoscope is still used at the same time. Therefore, the retinoscope is still a very important examining tool in optometry.

DISCLOSURE

Technical Problem

The present invention is directed to providing a retinoscope which may not only maintain a predetermined distance between an eye of an examinee and a retinoscopy lens but also maintain a predetermined distance for an optometric examination between the examinee and the retinoscope, and minimize spherical aberration by making an examination as near the line of sight of the examinee as possible, thereby allowing deriving an objective and accurate examination value.

In addition, the present invention is directed to providing a retinoscope having a camera mounted on a light beam projection ball of the retinoscope, which scans incident light beams projected into an eye of an examinee and reflected light beams and displays the scanned image so that an examiner diagnoses and corrects refractive errors of the eye of the examinee through the displayed image, thereby improving convenience of examination and facilitating manipulation based on a simple construction.

Technical Solution

One aspect of the present invention provides a retinoscope including: a refractor that includes a lens module in which a plurality of lenses necessary for correction are selectively located on an optometry window for obtaining a correction value for correcting an eye of an examinee and that is located at a predetermined distance in front of the eye of the examinee such that a line of sight of the examinee passes through the optometry window; a main body which is configured to support the refractor; a retinoscope unit which is coupled to one surface of the main body to maintain a predetermined distance from the refractor, projects light beams to the eye of the examinee near the line of sight of the examinee, and rotates or reciprocates the light beams upon receiving a signal from a control panel; and the control panel which is configured to manipulate operations of the refractor and the retinoscope unit.

The retinoscope may further include a camera unit mounted on the retinoscope unit to scan incident light beams projected into the eye of the examinee and reflected light beams reflected from a pupil and a display unit which receives an image scanned and transmitted by the camera unit and displays the image.

The refractor may be coupled to the main body to be movable forward and backward such that distance from the eye of the examinee is adjustable.

The main body may include a supporting rod which stands vertically on one side and has a guide hole formed in an upper end part of the supporting rod to be opened in a direction of the line of sight of the examinee, and a length adjusting bar which is slidably coupled to the guide hole for adjusting length. The refractor is coupled to the length adjusting bar to be movable forward and backward.

A guide bar may be further provided on the length adjusting bar of the main body in a perpendicular direction, and the refractor is slidably coupled to the guide bar to be movable in a direction perpendicular to the line of sight of the examinee.

A jaw holder may be configured to hold the face of the examinee is provided on the supporting rod such that the eye of the examinee is located at rear side of an optometry window of the refractor, and the jaw holder is provided to be adjustable in height.

The retinoscope unit may have one end rotatably coupled to one surface of the main body so as to rotate left and right with respect to the direction of the line of sight of the examinee.

The retinoscope unit may include a rotating member which has one end rotatably coupled to one surface of the main body and a length that is adjustable so as to maintain a predetermined distance from the refractor, a supporting member which stands vertically on and is rotatably coupled to the other end of the rotating member and has a height that is adjustable, and a retinoscope part which is coupled to an upper end of the supporting member to project light beams and rotates or reciprocates the light beams upon receiving a signal from the control panel.

The retinoscope part may include a lamp which generates a light source, a projection lens which converts the light source generated by the lamp into light beams, a reflector which reflects and projects the light beams into the eye of the examinee, an adjusting unit which rotates the lamp to adjust a direction of the light beams upon receiving a signal from the control panel, and a driving unit which induces the lamp to reciprocate in a direction perpendicular to a longitudinal direction of a filament of the lamp.

The adjusting unit may include a rotating structure which supports the lamp to be movable reciprocally and allows the driving unit to be mounted thereon, and a driving motor which rotates the rotating structure upon receiving a signal from the control panel.

The driving unit may include a driving motor which is provided in the direction perpendicular to the longitudinal direction of the filament of the lamp and is driven by receiving a signal from the control panel, and a cam which is coupled to a shaft of the driving motor and induces the lamp to reciprocate in the direction perpendicular to the longitudinal direction of the filament.

The retinoscope may further include a first sensing unit which detects movement of incident light beams projected into the eye of the examinee and movement of reflected light beams of the incident light beams reflected from the pupil of the examinee, a second sensing unit which detects brightness of the reflected light beams, and a controller which determines co-directional motion and counter-directional motion of the incident light beams and the reflected light beams according to the detected signal of the first sensing unit and detects time when the reflected light beams become the brightest according to the detected signal of the second sensing unit to automatically find a neutral point.

Advantageous Effects

According to one embodiment of the present invention, a retinoscope can maintain a predetermined distance between an eye of an examinee and a retinoscopy lens and can further maintain a predetermined distance for an optometric examination between the examinee and a retinoscope part. There is also an effect of minimizing spherical aberration as the examination is performed as near the line of sight of the examinee as possible, thereby allowing deriving an objective and accurate examination value.

Further, a high-definition camera is mounted on a rear side of an aperture of the retinoscope part to scan incident light beams projected into the an eye of the examinee and reflected light beams reflected from a pupil, and a scanned image is displayed so that an examiner diagnoses and corrects refractive errors of the eye of the examinee through the displayed image, thereby improving convenience of an examination.

Further, in comparison to the fact that an angle of astigmatism axis could not been accurately identified because a conventional examiner had to hold a retinoscope part by hand for the examination, the retinoscope part in a fixed state allows checking an inclined angle of light beam axis, thereby accurately identifying an astigmatism axis, leading to an effect that a correction value is accurately derived accordingly.

Further, an accurate value can be obtained by performing an objective examination, which is distinguished from the examination that has been done in a subjective manner and which could only be performed by a skilled person with a long-term training.

MODES OF THE INVENTION

Figure 1:
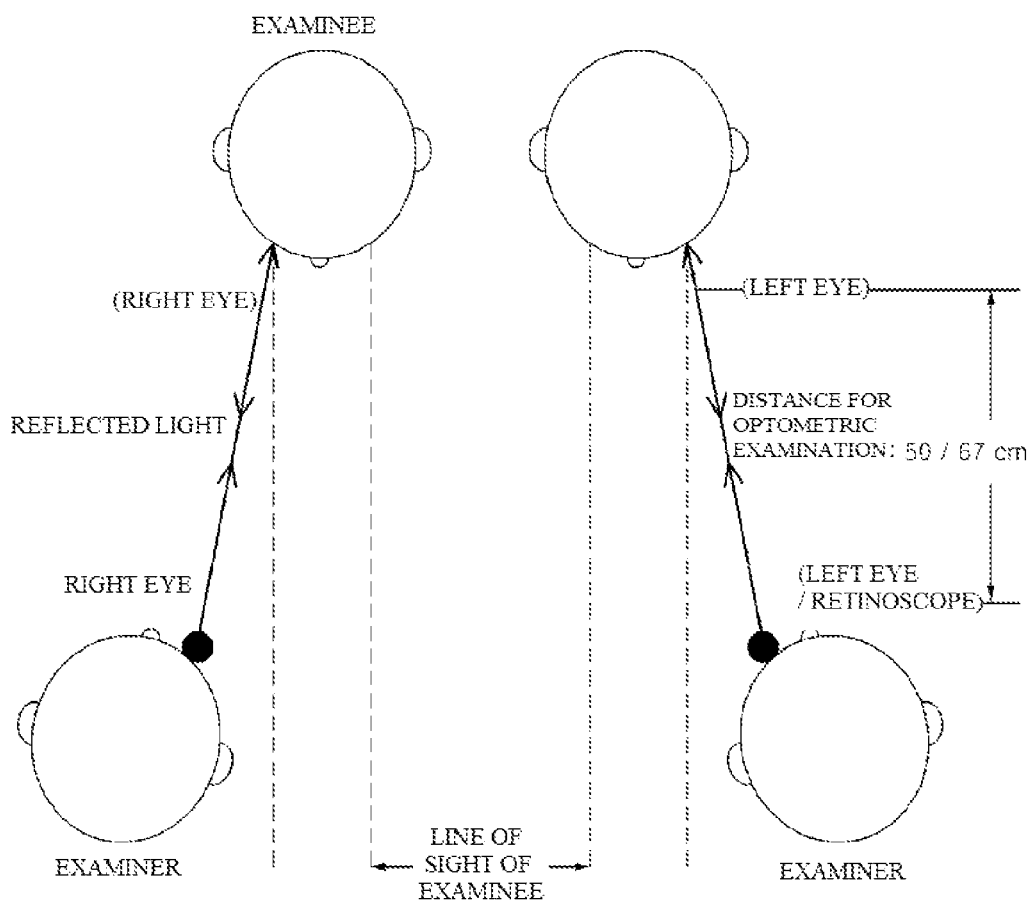
FIG. 1 is a conceptual diagram illustrating a refraction examination using a conventional retinoscope.

The above objectives, features, and other advantages of the present invention will become more apparent by describing in detail exemplary embodiments thereof in connection with the accompanying drawings. Hereinafter, exemplary embodiments of a retinoscope of the present invention will be described in detail with reference to the accompanying drawings. For this description, like reference numerals are used for like components unless otherwise described.

Figure 2:
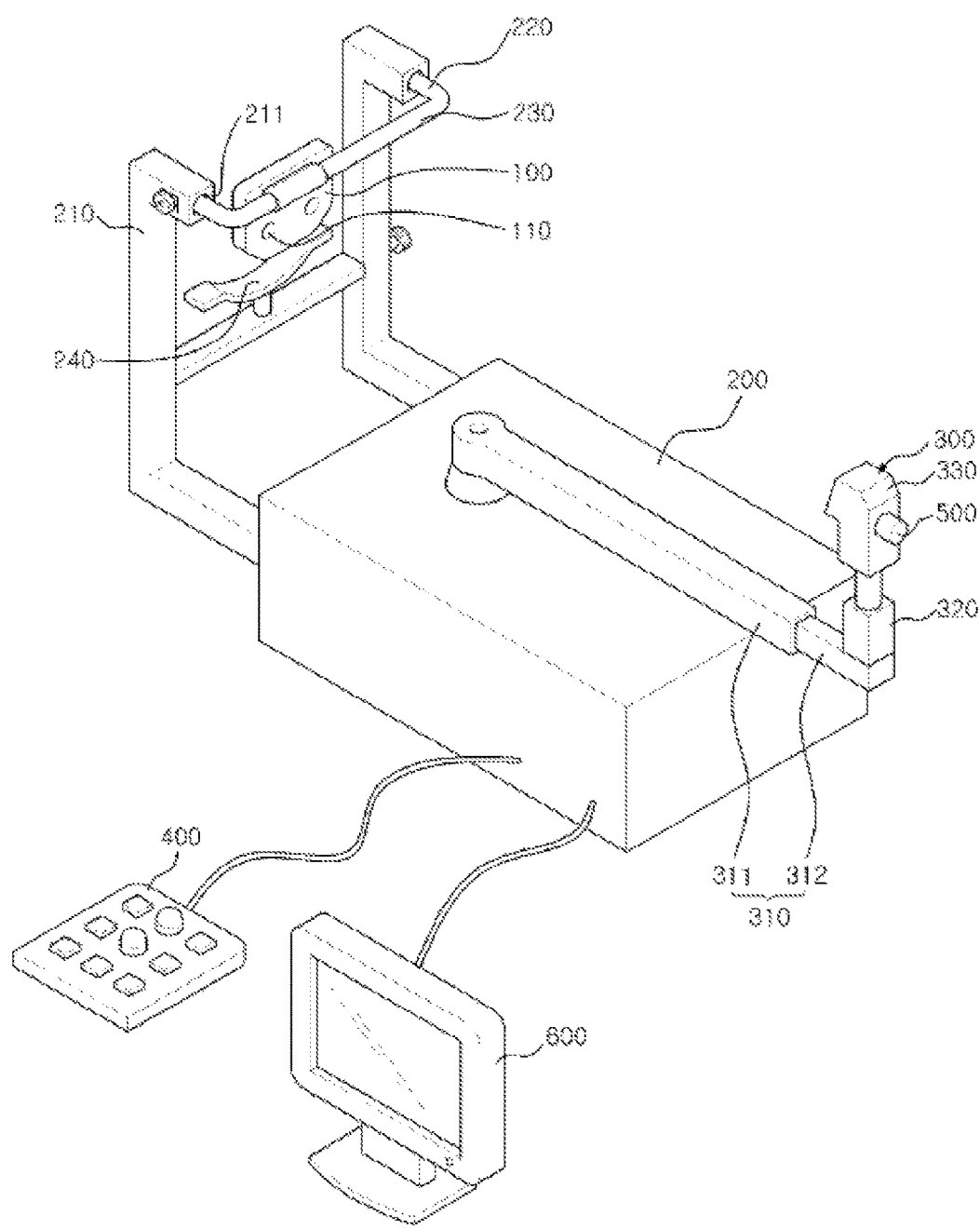
FIG. 2 is a perspective view illustrating a retinoscope according to one embodiment of the present invention.
Figure 3:
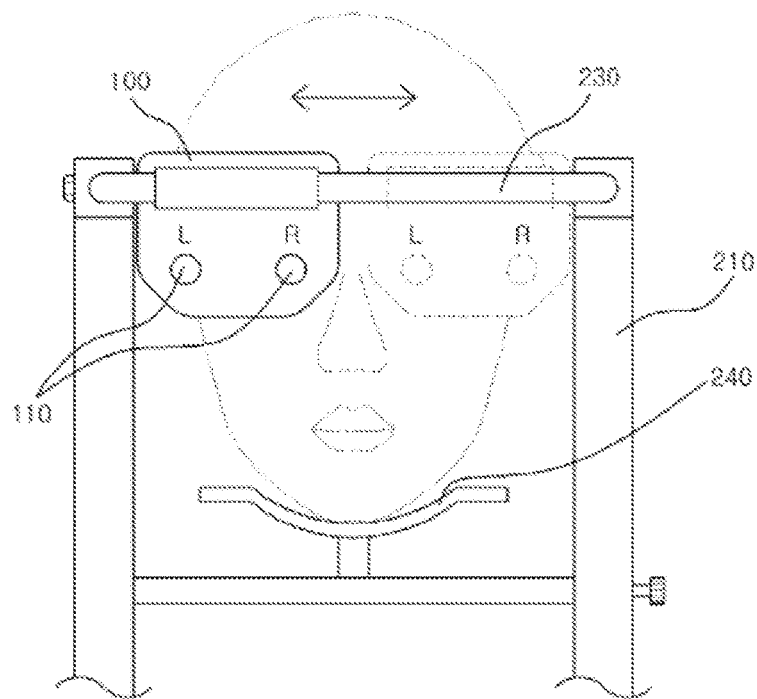
FIG. 3 is a front view illustrating a state in which a refractor of the retinoscope according to one embodiment of the present invention is moved laterally.
Figure 4:
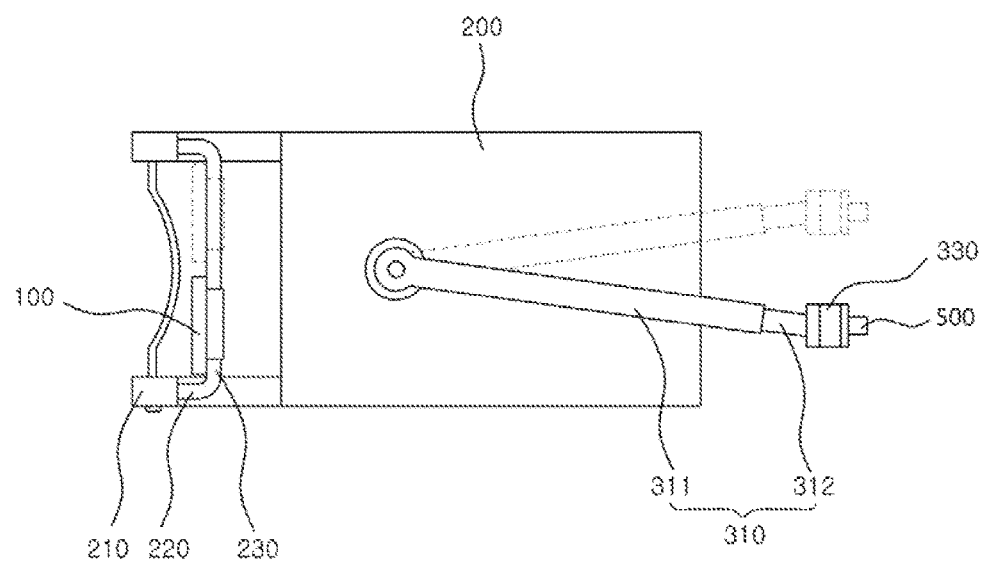
FIG. 4 is a plan view for describing a rotating member of a retinoscope part in the retinoscope according to one embodiment of the present invention.
Figure 5:
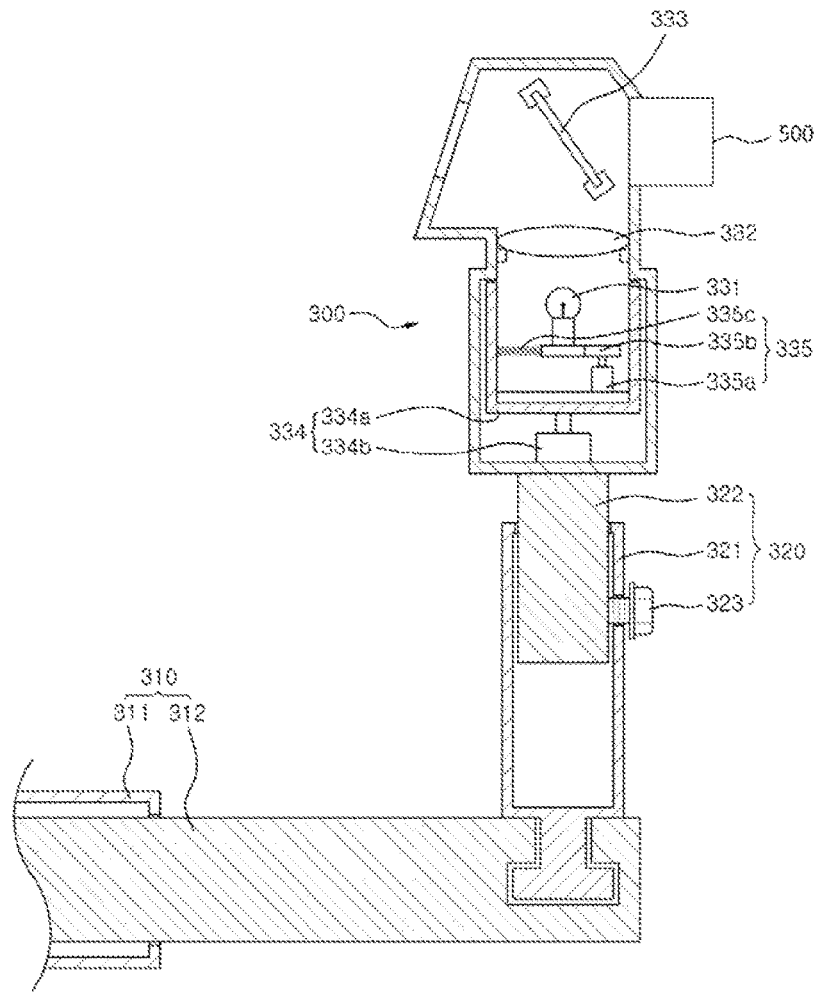
FIG. 5 is a cross-sectional view schematically illustrating the retinoscope part in the retinoscope according to one embodiment of the present invention.
Figure 6:
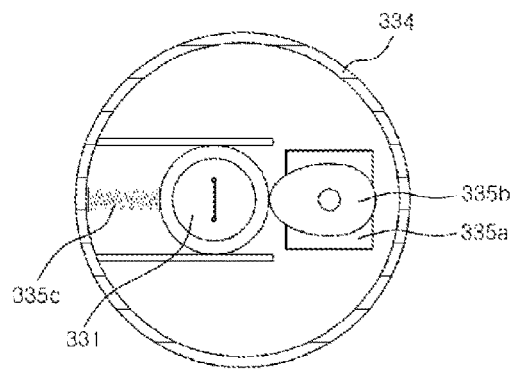
FIG. 6 is a cross-sectional view for describing a driving unit which reciprocates a lamp of the retinoscope part in the retinoscope according to one embodiment of the present invention.

FIG. 2 is a perspective view illustrating a retinoscope according to one embodiment of the present invention, FIG. 3 is a front view illustrating a state in which a refractor of the retinoscope according to one embodiment of the present invention is moved laterally, and FIG. 4 is a plan view for describing a rotating member of a retinoscope part in the retinoscope according to one embodiment of the present invention. Further, FIG. 5 is a cross-sectional view schematically illustrating the retinoscope part in the retinoscope according to one embodiment of the present invention, and FIG. 6 is a cross-sectional view for describing a driving unit which reciprocates a lamp of the retinoscope part in the retinoscope according to one embodiment of the present invention.

In one embodiment of the present invention, a side to which a line of sight of an examinee is oriented is considered as the front side for illustration.

As shown in FIGS. 2 to 6, the retinoscope according to one embodiment of the present invention is configured to include a refractor 100, a main body 200, a retinoscope unit 300, a control panel 400, a camera unit 500, and a display unit 600.

The refractor 100 is provided with a single or a plurality of optometry windows 110 and includes a lens module (not shown) in which a plurality of retinoscopy lenses necessary for correction are selectively located on the optometry window 110 for obtaining a correction value for correcting an eye of an examinee.

Here, in the lens module (not shown), the retinoscopy lens including approximately 55 lenses are configured to be rotated by an operation of a driving unit, and the driving unit is configured to be driven according to a signal from the control panel 400 to locate the retinoscopy lens at the optometry window 110. Here, when the plurality of optometry windows 110 are provided matching to left and right eyes of the examinee, the lens module is provided between the optometry windows 110 which are formed on left and right sides such that the rotating retinoscopy lens is located at the optometry windows 110 on left and right sides.

The refractor 100 with these configurations is coupled to the main body 200 to be movable forward and backward.

The main body 200 includes a supporting rod 210 which stands vertically on one side, and a length adjusting bar 220 which is slidably coupled to the supporting rod 210 in a perpendicular direction.

Here, the supporting rod 210 has an upper end part bent toward the front side to have a predetermined length and a guide hole 211 opened to the front side formed therein. Further, the length adjusting bar 220 is slidably coupled to the guide hole 211 of the support rod and is withdrawn to outside of the guide hole 211 for adjusting length.

Further, the refractor 100 is coupled to the length adjusting bar 220 to be moved forward and backward as the length adjusting bar 220 moves, thereby making distance between an eye of the examinee and the retinoscopy lens adjustable.

As shown in FIG. 3, the refractor 100 may be coupled to the main body 200 to be laterally movable so that the left and right eyes of the examinee may be examined sequentially or selectively. That is, as the refractor 100 is moved to left or right sides, the eyes of the examinee are examined sequentially or selectively.

Here, in terms of left and right movements of the refractor 100, a guide bar 230 is further provided in a direction perpendicular to the length adjusting bar 220 of the main body 200, and the refractor 100 is slidably coupled to the guide bar 230 to be movable in a direction perpendicular to a direction of a line of sight of the examinee.

More preferably, as shown in FIGS. 2 and 3, the supporting rod 210 having the length adjusting bar 220 is provided as a pair on the left and right at one side of the main body 200, the guide bar 230 is connected between the length adjusting bars 220 on the left and right, and the refractor 100 is slidably coupled to the guide bar 230 to be movable in the direction perpendicular to the direction of the line of sight of the examinee. Accordingly, in a state in which the face of the examinee is fixed, the refractor 100 is moved to left or right sides for examining the eyes of the examinee sequentially or selectively.

Furthermore, on the supporting rod 210, a jaw holder 240 may be provided to hold the face of the examinee such that the eye of the examinee is located in rear side of the optometry window 110 of the refractor 100. Here, the jaw holder 240 may be configured to be adjustable in length such that the eye of the examinee is horizontally located with the optometry window 110 of the refractor 100 in accordance with a size of the face of the examinee.

The retinoscope unit 300 is coupled to one surface of the main body 200 to maintain a predetermined distance from the refractor 100 and projects light beams to the eye of the examinee near the line of sight of the examinee.

The retinoscope unit 300 is configured to include a rotating member 310 which has one end rotatably coupled to an upper surface of the main body 200 and a length that is adjustable so as to maintain a predetermined distance from the refractor 100, a supporting member 320 which stands vertically on and is rotatably coupled to the other end of the rotating member 310 and has a height that is adjustable, and a retinoscope part 330 which is coupled to an upper end of the supporting member 320 to project light beams.

As shown in FIG. 4, with the plan view as a reference, the rotating member 310 rotates in the left and right sides in the direction of the line of sight of the examinee such that the line of sight of the eye subjected to the examination and light beams are located near a horizontal line according to the left eye or the right eye of the examinee subjected to the examination.

In addition, the rotating member 310 includes a first member 311 which has one end rotatably coupled to the upper surface of the main body 200 and a second member 312 which is withdrawn outside while being accommodated inside the first member 311 so that a length is adjustable, and thus, a distance between the eye of the examinee and the retinoscope part 330 becomes adjustable. At this point, in terms of adjusting length of the rotating member 310, the distance between the eye of the examinee and the retinoscope part 330 may be adjustable from 30 cm to 1 m.

Standing in a direction perpendicular to the rotating member 310 and serving to support the retinoscope part 330, the supporting member 320 is rotatably coupled to the rotating member 310. That is, when the rotating member 310 rotates in the left and right to a rotating axis, the retinoscope part 330 supported by the supporting member 320 which stands vertically on the rotating member 310 also moves according to a radius of rotation such that an angle in which the light beams are projected is twisted. Here, by rotating the supporting member 320 to correct the twisted angle of the retinoscope part 330, the light beams to be projected are projected to the eye of the examinee.

In addition, the supporting member 320 is provided to be adjustable in height. That is, the supporting member is provided to be adjustable in height such that the light beams of the retinoscope part 330 are projected as near the line of sight of the examinee as possible matching to an eye height of the examinee.

Here, in terms of adjusting height of the supporting member 320, the height may be adjustable by a first member 321 which has an accommodating unit formed therein, a second member 322 which is withdrawn outside while being accommodated in the accommodating unit and has the retinoscope part 330 coupled to an upper surface thereof, and a clamping member 323 which presses the second member 322 at an outer surface of the first member 321 to secure the adjusted length.

As shown in FIG. 5, while the retinoscope part 330 is configured to have the same constitution as a conventional retinoscope part including a lamp 331, a projection lens 332, and a reflector 333, the retinoscope part may further include an adjusting unit 334 which rotates the lamp 331 to adjust a direction of the light beams upon receiving a signal from the control panel 400, and a driving unit 335 which induces the lamp 331 to reciprocate in a direction perpendicular to a longitudinal direction of a filament upon receiving the signal from the control panel 400.

As shown in FIG. 6, the adjusting unit 334 is configured to include a rotating structure 334a which accommodates the lamp and supports the lamp 331 to be movable reciprocally, and a driving motor 334b which rotates the rotating structure 334a upon receiving a signal from the control panel 400. When axes of incident light beams and reflected light beams reflected from a pupil are not matched in a straight line, such adjusting unit 334 adjusts direction of the lamp to rotate the light beams so that the axes are matched.

Further, the driving unit 335 inducing the lamp to reciprocate is configured to include a driving motor 335a which is provided at one side of the lamp 331 in the direction perpendicular to the longitudinal direction of the filament of the lamp 331 and is mounted on the rotating structure 334a and driven by receiving a signal from the control panel 400, a cam 335b which is coupled to a shaft of the driving motor 335a and pushes the lamp in the direction perpendicular to the longitudinal direction of the filament in order to induce reciprocation, and an elastic spring 335c which is fixed at an inner wall of the rotating structure to support the other side of the lamp 331.

Further, in the driving unit 335 inducing the lamp 331 to reciprocate, when the driving motor 335a is driven by receiving the signal from the control panel 400, the cam 335b coupled to the driving shaft pushes the lamp 331 while rotating such that the lamp 331 is induced to reciprocate, thereby reciprocating the light beams.

Here, for the lamp 331, a halogen bulb is mostly used currently, but a light emitting diode (LED) or a laser which is adjusted to be harmless to eyes may be used. Currently, a bulb with a linear filament is used for a retinoscope part, which is advantageous to form the incident light beams of a linear type. Accordingly, it is preferable for the LED to be manufactured in a linear emissive configuration by densely stacking a plurality of single emissive configurations. For the laser, after light beams are emitted and weakened to such an extent to be harmless to the eyes, it is preferable to emit linear light beams through a linear aperture. Further, in the halogen bulb, the LED, and the laser, chromatic aberration may be occurred according to color, and calibration may be necessary according to color of a light source because increasingly redder color indicates increasingly hyperopic result.

The control panel 400 is electrically connected to the refractor 100 and the retinoscope unit 300, and manipulates operations of the refractor 100 and the retinoscope unit 300.

That is, the control panel 400 is provided with various types of switch and manipulating lever for turning a power supply of the retinoscope part on or off, turning light beams of the retinoscope part on or off, turning the driving unit of the retinoscope part on or off, adjusting width of linear light beams, adjusting convergent light beams and divergent light beams, adjusting axis, turning a power supply of the refractor on or off, and adjusting operation of the lens module of the refractor.

Further, the camera unit 500 is mounted at rear side of an aperture of the retinoscope part 330 such that the camera unit scans an image of incident light beams projected into the eye of the examinee and reflected light beams reflected from the pupil and transmits the scanned image to the display unit 600.

Further, the display unit 600 receives the image scanned by the camera unit 500 to display the images on a screen window. Thus, since an examiner diagnoses and corrects refractive errors of the eye of the examinee through the displayed images, not only eye strain of the examiner is reduced but also convenience of examination is improved.

Further, the retinoscope according to one embodiment of the present invention may be configured to further include a first sensing unit, a second sensing unit, and a controller, but detailed illustrations with respect to the first sensing unit, the second sensing unit, and the controller are omitted.

The first sensing unit detects movement of incident light beams which are projected from the retinoscope unit 300 into the eye of the examinee and movement of reflected light beams of the incident light beams which are reflected from the pupil of the examinee. The second sensing unit detects brightness of the reflected light beams.

Further, the controller determines co-directional motion and counter-directional motion of the incident light beams and the reflected light beams according to the detected signal of the first sensing unit and detects time when the reflected light beams become the brightest according to the detected signal of the second sensing unit to automatically find a neutral point.

Accordingly, the retinoscope may find the neutral point more accurately and rapidly.

An examination method using the retinoscope configured as above is described below.

First, a face of the examinee is put on the jaw holder 240, the refractor 100 is located in front of the right eye of the examinee, and then distance of the refractor 100 is adjusted such that distance between the right eye of the examinee and the retinoscopy lens of the refractor 100 is maintained in a range of 10 mm to 15 mm.

Further, the examinee is instructed to keep the eye on an eye chart such that the line of sight of the examinee passes through the optometry window 110. Here, for an Asian person, it is preferable that the distance between the eye of the examinee and the retinoscopy lens of the refractor 100 is maintained about 12 mm. When the eye of the examinee is not located at the optometry window, height of the jaw holder 240 for face may be adjusted for locating the eye of the examinee at the optometry window.

After the distance between the right eye of the examinee and the refractor 100 is adjusted, the rotating member 310 of the retinoscope unit is rotated such that the retinoscope part 330 is located near a horizontal line of the optometry window of the right eye.

Then, by rotating the supporting member 320, an angle of the retinoscope part 330 which is twisted due to a rotation radius of the rotating member 310 is adjusted. That is, as the supporting member 320 is rotated, light beams projected from the retinoscope part are projected toward the right eye of the examinee.

Further, height of the supporting member 320 is adjusted such that the light beams are projected as near the line of sight of the examinee as possible. Then, by adjusting length of the rotating member 310, a distance for an optometric examination is adjusted such that the retinoscope part 330 is located at an optimum distance for an optometric examination from the eye of the examinee. Here, the distance for an optometric examination is adapted for convenience of the examiner, and a calibration value is differentiated by the distance for an optometric examination. For example, when the distances for an optometric examination are 50 cm, 67 cm, and 1 m, calibration values of 2 D, 1.5 D, and 1 D are applied, respectively.

Further, when dynamic retinoscopy is used to obtain a refractive power of a myopia correction lens, it is preferable to maintain a distance for an optometric examination approximately in a range of 30 cm to 40 cm.

Then, after convergent light beams or divergent light beams, width of light beams, etc. of the retinoscope part 330 are adjusted, linear light beams are projected to the right eye of the examinee. Here, the convergent light beams or the divergent light beams, the width of light beams, etc. may be adjusted by the control panel 400.

Then, the camera unit 500 scans an image of the incident light beams, which are projected to the right eye and the reflected light beams which are reflected by and exited from the pupil, and transmits the image to the display unit 600. Further, the examiner manipulates the control panel 400 to find a neutral point while checking the image displayed on the display unit 600.

Hereinafter, an example in which an examination value is calculated based on projecting linear light beams adjusted by the divergent light beams at a distance for an optometric examination of 50 cm.

When axes of the incident light beams projected to the right eye and the reflected light beams reflected from the pupil are not matched in a straight line, the axis of the incident light beams has to be matched to the axis of the reflected light beams. Here, in terms of a method of matching the axes, a signal is applied from the control panel to rotate the adjusting unit, the incident light beams are matched to the axis of the reflected light beams by adjusting direction of the light beams, and then a numerical value of the rotated angle is checked.

Then, when the axes of the incident light beams and the reflected light beams are matched, the incident light beams are moved in a direction perpendicular to an axial direction. Here, in terms of movement of the incident light beams, the driving unit 335 driven upon receiving the signal from the control panel 400 induces the lamp 331 to reciprocate, thereby reciprocating the light beams.

Then, the movements of the incident light beams and the reflected light beams are observed for determining co-directional motion and counter-directional motion with respect to each other. Here, while a streak of the incident light beams and a streak of the reflected light beams move in the same direction in the co-directional motion, the streak of the incident light beams and the streak of the reflected light beams move in the opposite direction in the counter-directional motion. Then, when the movements of the incident light beams and the reflected light beams are the counter-directional motion, the examiner increases power of the retinoscopy lens of the refractor by one step at a time (a unit of 0.25 D) in the negative direction. The same work is repeated until the co-directional motion is achieved.

Then, when the co-directional motion is achieved, the power of the retinoscopy lens is changed by one step at a time in the positive direction again to find a neutral point between the co-directional motion and the counter-directional motion. Here, at the neutral point, the reflected light beams are shown the brightest. Even though the light beams are reciprocated, there is no movement in the reflected light beams.

At the neutral point, a power value of the lens of the refractor is obtained. Here, the obtained power of the lens is a refractive error value of the examinee. In addition, for a person with astigmatism, the incident light beams are changed in a perpendicular direction at the neutral point initially found, and then a neutral point needs to be found once more.

Here, when the axis of the reflected light beams and the axis of the incident light beams are not matched but dislocated, the condition is known as astigmatism. In the case of astigmatism, the incident light beams are changed in a perpendicular direction at the neutral point initially found. By repeating the above procedure, a neutral point may be found, and then a power value of the lens of the refractor at the neutral point may be obtained.

For example, when first vertical incident light beams ↕ have an axial direction of 180 degrees and are neutralized for reciprocation in a direction of 90 degrees by −5.00 D, and the incident light beams are changed in a perpendicular direction such that the lateral incident light beams ↔ an axial direction of 90 degrees and are neutralized for reciprocation in a direction of 180 degrees by −3.50 D, a power value of the lens of the refractor may be calculated using a spherical lens, a cylindrical lens, and an axis as below.

3.50 D-1.50 D*180

2.00 D (a calibration value of examination distance)

5.50 D-1.50 D*180

On the other hand, in the case of myopia, an examination with moving in a direction from a high-minus power to a low-minus power using divergent light beams may be more precise, and in the case of hyperopia, an examination with moving in a direction from a high-plus power to a low-plus power using convergent light beams may be performed.

Further, in the examination above, from the movements of the incident light beams and the reflected light beams, co-directional motion and counter-directional motion with respect to each other may be found using software such as a motion tracker. Then, after detecting the time when the reflected light beams become the brightest with a piece of software detecting brightness of the reflected light beams, a neutral point is searched by analyzing the two pieces of software, thereby more precisely and easily finding a neutralization value.

When the examination of the right eye is complete based on the above method, the refractor 100 is moved to the left side such that the optometry window 110 of the refractor is located in front of the left eye of the examinee.

Then, the rotating member 310 is rotated such that the retinoscope part 330 is located near a horizontal line of the optometry window 110 of the left eye of the examinee.

Then, the supporting member 320 is rotated to adjust an angle of the retinoscope part 330 which is twisted due to a rotation radius of the rotating member 310. That is, the supporting member 320 is rotated so that light beams projected from the retinoscope part are projected toward the left eye of the examinee.

Then, after adjusting convergent light beams or divergent light beams, width of light beams, etc. of the retinoscope part 330, linear light beams are projected to the left eye of the examinee. Here, the camera unit 500 scans an image of the incident light beams, which are projected to the left eye and the reflected light beams which are reflected by and exited from the pupil, and transmits the image to the display unit 600.

The examiner checks the image displayed on the display unit 600 and finds a neutral point of the left eye by manipulating the control panel 400 using the above method.

The retinoscope as configured above may be manually adjusted in terms of adjustment of distance for an optometric examination, location adjustment of the retinoscope part, and location adjustment of the refractor during the examination. Also, the examination procedure after projecting light beams from the retinoscope may be completely automated to automatically calculate an examination value by using the motion tracker and brightness detecting software and interworking with adjustment of lens power of the refractor and reciprocation of light beams. A semi-automation in which axial direction adjustment, reciprocation of light beams, and refractor lens power adjustment are manually adjusted or adjusted by a manipulating part during the examination may also be applied.

As such, while a retinoscope of the present invention performs an examination based on the same method as a refraction examination using a conventional retinoscope, the examination is performed in a state in which a refractor and a retinoscope unit are fixated on a main body of the retinoscope. Thus, a predetermined distance between an eye of an examinee and a retinoscopy lens is maintained, and also, a predetermined distance for an optometric examination between the examinee and the retinoscope part is maintained. As the examination is performed as near a line of sight of the examinee as possible, spherical aberration is minimized, thereby allowing deriving an objective and accurate examination value.

Further, a high-definition camera is mounted on rear side of an aperture of the retinoscope part to scan incident light beams projected into an eye of the examinee and reflected light beams reflected from a pupil, a scanned image is displayed, and an examiner diagnoses and corrects refractive errors of the eye of the examinee through the displayed image, thereby improving convenience of the examination.

Further, while an angle of astigmatism axis has not been accurately identified conventionally because an examiner had to perform an examination while holding the retinoscope part by hand, the retinoscope part in a fixed state allows checking an inclined angle of light beam axis, thereby accurately identifying an astigmatism axis, leading to accurately deriving a correction value accordingly.

Further, an objective examination in which an accurate value can be obtained is performed rather than an examination in a subjective manner which could only be performed by a skilled person with a long-term training.

Further, as the refractor is moved to left or right sides, the eyes of the examinee are examined sequentially or selectively. Thus, the examinee feels less enclosed such that myopization by a device may be reduced.

The present invention may be widely used in a retinoscope.

While preferable embodiments of the present invention have been described above, the invention is not limited to the above-described specific exemplary embodiments. That is, those skilled in the art may variously modify and change the invention without departing from the scope and spirit of the present invention claimed by the appended claims, and all appropriate modifications and changes are considered to be equivalents that fall within the scope of the claims.

The invention claimed is:

1. An apparatus for retinoscopy comprising:
a refractor that includes a lens module in which a plurality of lenses necessary for correction are selectively located on an optometry window for obtaining a correction value for correcting an eye of an examinee and that is located at a predetermined distance in front of the eye of the examinee such that a line of sight of the examinee passes through the optometry window;
a main body couple to the refractor to support the refractor;
a retinoscope coupled to one surface of the main body to maintain a predetermined distance from the refractor, configured to project light beams to the eye of the examinee near the line of sight of the examinee, and configured to rotate or reciprocate the light beams upon receiving a an instruction/input from a control panel; and
the control panel electrically connected to the refractor and the retinoscope to manipulate operations of the refractor and the retinoscope,
wherein the retinoscope includes:
a rotating member which has one end rotatably coupled to one surface of the main body so that other end is configured to rotate radially and a length that is adjustable so as to adjust a horizontal distance between the refractor and retinoscope;

a retinoscope part configured to project light beams and configured to rotate or reciprocate the light beams according to the instruction/input from the control panel; and a supporting member which stands vertically on and is rotatably coupled to the other end of the rotating member so as to support the retinoscope part and adjust a height of the retinoscope part, and configured to rotate the retinoscope part so as to adjust an angle of the retinoscope part according to a rotation of the rotating member.

2. The apparatus of claim 1, further comprising:
a camera mounted on the retinoscope to scan incident light beams projected into the eye of the examinee and reflected light beams reflected from a pupil; and
a display configured to receive an image scanned and transmitted by the camera and display the image.

3. The apparatus of claim 1, wherein the refractor is coupled to the main body to be movable forward and backward such that distance from the eye of the examinee is adjustable.

4. The apparatus of claim 3, wherein the main body comprises a supporting rod which stands vertically on one side and has a guide hole formed in an upper end part to be opened in a direction of the line of sight of the examinee, and a length adjusting bar which is slidably coupled to the guide hole for adjusting length, wherein the refractor is coupled to the length adjusting bar to be movable forward and backward.

5. The apparatus of claim 4, wherein a guide bar is further provided on the length adjusting bar of the main body in a perpendicular direction, and the refractor is slidably coupled to the guide bar to be movable in a direction perpendicular to the line of sight of the examinee.

6. The apparatus of claim 4, wherein a jaw holder configured to hold the face of the examinee is provided on the supporting rod such that the eye of the examinee is located at rear side of an optometry window of the refractor, and the jaw holder is provided to be adjustable in height.

7. The apparatus of claim 1, wherein the retinoscope has one end rotatably coupled to one surface of the main body to rotate left and right with respect to the direction of the line of sight of the examinee.

8. The apparatus of claim 1, wherein the retinoscope part is configured to comprise:
a lamp configured to generate a light source;
a projection lens configured to convert the light source generated by the lamp into light beams;
a reflector configured to reflect and project the light beams into the eye of the examinee;
an adjusting member configured to rotate the lamp to adjust a direction of the light beams upon receiving the instruction/input from the control panel, and
a driving member configured to induce the lamp to reciprocate in a direction perpendicular to a longitudinal direction of a filament of the lamp.

9. The apparatus of claim 8, wherein the adjusting member is configured to comprise a rotating structure which supports the lamp to be movable reciprocally and allows the driving member to be mounted thereon, and a driving motor which rotates the rotating structure upon receiving the instruction/input from the control panel.

10. The apparatus of claim 9, wherein the driving member is configured to comprise a driving motor which is provided in the direction perpendicular to the longitudinal direction of the filament of the lamp and is driven by receiving the instruction/input from the control panel, and a cam which is coupled to a shaft of the driving motor and induces the lamp to reciprocate in the direction perpendicular to the longitudinal direction of the filament.

\* \* \* \* \*